United States Patent [19]

Johnson

[11] 4,245,087
[45] Jan. 13, 1981

[54] 9-DEOXY-5,9α-EPOXY-5,6-DIDEHYDRO-PGF₁ AMIDES

[75] Inventor: Roy A. Johnson, Kalamazoo, Mich.

[73] Assignee: The Upjohn Company, Kalamazoo, Mich.

[21] Appl. No.: 73,576

[22] Filed: Sep. 7, 1979

Related U.S. Application Data

[60] Division of Ser. No. 932,899, Aug. 11, 1978, which is a division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.³ .............................................. C07D 311/02
[52] U.S. Cl. .................................. 542/420; 260/345.2; 542/421; 542/426; 542/429; 424/283
[58] Field of Search ..................... 260/345.2; 542/420, 542/421, 426, 429

[56] References Cited

U.S. PATENT DOCUMENTS 4,125,713  11/1978  Nelson ................................ 542/426

Primary Examiner—Nicky Chan
Attorney, Agent, or Firm—Robert A. Armitage

[57] ABSTRACT

The present invention relates to novel 9-deoxy-5,9α-epoxy-5,6-didehydro-PGF₁ amides, which are useful for inducing a variety of prostacyclin-like pharmacological effects. Accordingly, these compounds are useful pharmacological agents for the same purposes for which prostacyclin is employed.

41 Claims, No Drawings

9-DEOXY-5,9α-EPOXY-5,6-DIDEHYDRO-PGF₁ AMIDES

CROSS REFERENCE TO RELATED APPLICATION

The present application is a divisional application of U.S. Pat. No. 932,899, filed Aug. 11, 1978, now pending issuance as a U.S. patent; which is a divisional application of U.S. Ser. No. 819,856, filed July 28, 1977, now U.S. Pat. No. 4,123,441; which is a continuation-in-part application of U.S. Ser. No. 725,546, filed Sept. 22, 1976, now abandoned; which is a continuation-in-part application of U.S. Ser. No. 716,960, filed Aug. 23, 1976, now abandoned.

BACKGROUND OF THE INVENTION

The present invention relates to novel 9-deoxy-5,9α-epoxy-5,6-didehydro-PGF₁ amides, which are useful for inducing a variety of prostacyclin-like pharmacological effects. Accordingly, these compounds are useful pharmacological agents for the same purposes for which prostacyclin is employed.

The essential material constituting a disclosure of the preparation and use of the novel compounds of the present invention is incorporated here by reference from U.S. Pat. No. 4,123,441.

SUMMARY OF THE INVENTION

The present invention particularly provides:
a 4Z compound of the formula

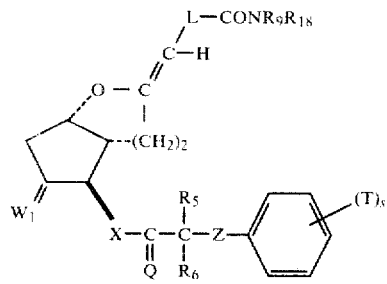

wherein $W_1$ is α-OH:β-H, α-H:β-OH, oxo, methylene, α-H:β-H, α-CH₂OH:β-H;

wherein L is —(CH₂)$_d$—C(R₂)₂, wherein d is zero to 5, $R_2$ is hydrogen, methyl, or fluoro, being the same or different with the proviso that one $R_2$ is not methyl when the other is fluoro;

wherein Q is oxo, α-H:β-H, α-OH:β-R₈ or α-R₈:β-OH wherein $R_8$ is hydrogen or alkyl of one to 4 carbon atoms, inclusive;

wherein $R_9$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—), a valence bond or alkylene of one to 9 carbon atoms, inclusive, with one to 6 carbon atoms, inclusive between CR₅R₆— and the phenyl ring;

wherein T is alkyl of one to 4 carbon atoms, inclusive, fluoro, chloro, trifluoromethyl, or —OR₇—, wherein $R_7$ is alkyl of one to 4 carbon atoms, inclusive, and s is zero, one, 2, or 3, with the proviso that not more than two T's are other than alkyl and when s is 2 or 3 the T's are either the same or different; and wherein X is
(1) trans—CH═CH—,
(2) cis—CH═CH—,
(3) —C≡C—, or
(4) —CH₂CH₂—;

including the lower alkanoates thereof; and a 4E compound of the formula

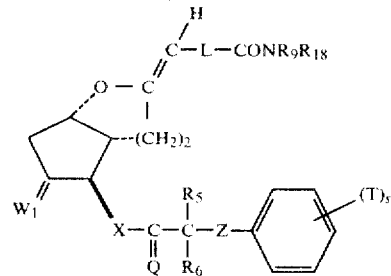

wherein $W_1$ is α-OH:β-H, α-H:β-OH, oxo, methylene, α-H:β-H, α-CH₂OH:β-H;

wherein L is —(CH₂)$_d$—C(R₂)₂, wherein d is zero to 5, $R_2$ is hydrogen, methyl, or fluoro, being the same or different with the proviso that one $R_2$ is not methyl when the other is fluoro;

wherein Q is oxo, α-H:β-H, α-OH:β-R₈ or α-R₈:β-OH wherein $R_8$ is hydrogen or alkyl of one to 4 carbon atoms, inclusive;

wherein $R_9$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); where Z represents an oxa atom (—O—), a valence bond or alkylene of one to 9 carbon atoms, inclusive, with one to 6 carbon atoms, inclusive between CR₅R₆- and the phenyl ring;

wherein T is alkyl of one to 4 carbon atoms, inclusive, fluoro, chloro, trifluoromethyl, or —OR₇—, wherein $R_7$ is alkyl of one to 4 carbon atoms, inclusive, and s is zero, one, 2, or 3, with the proviso that not more than two T's are other than alkyl and when s is 2 or 3 the T's are either the same or different; and wherein X is
(1) trans—CH═CH—,
(2) cis—CH═CH—,
(3) —C≡C—, or
(4) —CH₂CH₂—;

including the lower alkanoates thereof.

With regard to the divalent substituents described in the claims, e.g., Q and $W_1$, these divalent radicals are defined as α-R$_i$:β-R$_j$, where R$_i$ represents a substituent of the divalent moiety of the alpha configuration with respect to the cyclopentane and $R_j$ represents a substituent of the divalent moiety of the beta configuration with respect to the cyclopentane ring. Accordingly, when Q is defined as $\alpha\text{-OH}:\beta\text{-}R_8$, the hydroxy of the Q moiety is in the alpha configuration, i.e., as in prostacyclin, and the $R_8$ substituent is in the beta configuration. Not all carbon atoms to which such divalent moieties are attached represent asymmetric centers. For example, when both valence bonds are to hydrogen (e.g., $W_1$ or Q is $\alpha\text{-H}:\beta\text{-H}$), then no asymmetric center is present.

DESCRIPTION OF THE PREFERRED EMBODIMENTS

The present invention particularly relates to the following chemical compounds:

(4Z)-9-deoxy-5,9α-epoxy-Δ4-11-deoxy-16-phenoxy-17,18,19,20-tetranor-PGF$_1$, amide;

(4Z)-9-deoxy-5,9α-epoxy-Δ4-17-phenyl-18,19,20-trinor-13,14-didehydro-PGF$_1$, amide;

(4Z)-9-deoxy-5,9α-epoxy-Δ4-16-phenoxy-17,18,19,20-trinor-13,14-didehydro-PGF$_1$, amide;

(4Z)-9-deoxy-5,9α-epoxy-Δ4-13,14-dihydro-16-phenoxy-17,18,19,20-tetranor-PGF$_1$, amide;

(4Z)-9-deoxy-5,9α-epoxy-Δ4-17-phenyl-18,19,20-trinor-PGF$_1$, amide;

(4Z)-9-deoxy-5,9α-epoxy-Δ4-17-phenyl-18,19,20-trinor-cis-13-PGF$_1$, amide;

(4Z)-9-deoxy-5,9α-epoxy-Δ4-16-phenoxy-17,18,19,20-tetranor-cis-13-PGF$_1$, amide;

(4Z)-9-deoxy-5,9α-epoxy-Δ4-16-(m-trifluoromethylphenoxy)-17,18,19,20-tetranor-13,14-dihydro-PGF$_1$, amide;

(4Z)-9-deoxy-5,9α-epoxy-Δ4-16-(m-chlorophenoxy)-17,18,19,20-tetranor-13,14-dihydro-PGF$_1$, amide;

(4Z)-9-deoxy-5,9α-epoxy-Δ4-16-(p-fluorophenoxy)-17,18,19,20-tetranor-13,14-dihydro-PGF$_1$, amide;

(4Z)-9-deoxy-5,9α-epoxy-Δ4-16-(m-trifluoromethylphenoxy)-17,18,19,20-tetranor-PGF$_1$, amide;

(4Z)-9-deoxy-5,9α-epoxy-Δ4-16-(m-chlorophenoxy)-17,18,19,20-tetranor-PGF$_1$, amide;

(4Z)-9-deoxy-5,9α-epoxy-Δ4-16-(p-fluorophenoxy)-17,18,19,20-tetranor-PGF$_1$, amide;

(4Z)-9-deoxy-5,9α-epoxy-Δ4-16-(m-trifluoromethylphenoxy)-17,18,19,20-tetranor-cis-13-PGF$_1$, amide;

(4Z)-9-deoxy-5,9α-epoxy-Δ4-16,16-dimethyl-17-phenyl-18,19,20-trinor-13,14-dihydro-PGF$_1$, amide;

(4Z)-9-deoxy-5,9α-epoxy-Δ4-16,16-dimethyl-17-phenyl-18,19,20-trinor-PGF$_1$, amide;

(4Z)-9-deoxy-5,9α-epoxy-Δ4-16-methyl-16-phenoxy-18,19,20-trinor-PGF$_1$, amide;

(4Z)-9-deoxy-5,9α-epoxy-Δ4-16,16-dimethyl-17-phenyl-18,19,20-trinor-cis-13-PGF$_1$, amide;

(4Z)-9-deoxy-5,9α-epoxy-Δ4-16,16-difluoro-17-phenyl-18,19,20-trinor-13,14-dihydro-PGF$_1$, amide;

(4Z)-9-deoxy-5,9α-epoxy-Δ4-16,16-difluoro-17-phenyl-18,19,20-trinor-PGF$_1$, amide;

(4Z)-9-deoxy-5,9α-epoxy-Δ4-2,2-difluoro-16-phenoxy-17,18,19,20-tetranor-13,14-dihydro-PGF$_1$, amide;

(4Z)-9-deoxy-5,9α-epoxy-Δ4-2,2-difluoro-17-phenyl-18,19,20-trinor-PGF$_1$, amide;

(4Z)-9-deoxy-5,9α-epoxy-Δ4-2,2-difluoro-16-phenoxy-17,18,19,20-tetranor-PGF$_1$, amide;

(4Z)-9-deoxy-5,9α-epoxy-Δ4-2,2-difluoro-16-phenoxy-17,18,19,20-tetranor-cis-13-PGF$_1$, amide;

(4Z)-9-deoxy-5,9α-epoxy-Δ4-2,2-difluoro-16-methyl-16-phenoxy-18,19,20-trinor-13,14-dihydro-PGF$_1$, amide;

(4Z)-9-deoxy-5,9α-epoxy-Δ4-2,2-difluoro-16-methyl-16-phenoxy-18,19,20-trinor-PGF$_1$, amide; and (4Z)-9-deoxy-5,9α-epoxy-Δ4-2,2-difluoro-16-methyl-16-phenoxy-18,19,20-trinor-cis-13-PGF$_1$, amide.

I claim:

1. A compound of the formula

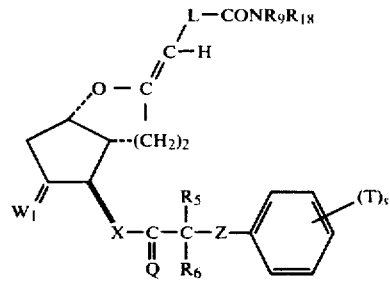

wherein $W_1$ is $\alpha\text{-OH}:\beta\text{-H}$, $\alpha\text{-H}:\beta\text{-OH}$, oxo, methylene, $\alpha\text{-H}:\beta\text{-H}$, $\alpha\text{-CH}_2\text{OH}:\beta\text{-H}$;

wherein L is $-(CH_2)_d-C(R_2)_2$, wherein d is zero to 5, $R_2$ is hydrogen, methyl, or fluoro, being the same or different with the proviso that one $R_2$ is not methyl when the other is fluoro;

wherein Q is oxo, $\alpha\text{-H}:\beta\text{-H}$, $\alpha\text{-OH}:\beta\text{-R}_8$ or $\alpha\text{-R}_8:\beta\text{-OH}$ wherein $R_8$ is hydrogen or alkyl of one to 4 carbon atoms, inclusive;

wherein $R_9$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—), a valence bond or alkylene of one to 9 carbon atoms, inclusive, with one to 6 carbon atoms, inclusive between $CR_5R_6$— and the phenyl ring; wherein T is alkyl of one to 4 carbon atoms, inclusive, fluoro, chloro, trifluoromethyl, or —OR$_7$—, wherein $R_7$ is alkyl of one to 4 carbon atoms, inclusive, and s is zero, one, 2, or 3, with the proviso that not more than two T's are other than alkyl and when s is 2 or 3 the T's are either the same or different; and wherein X is (1) trans—CH=CH—,
(2) cis—CH=CH—,
(3) —C≡C—, or
(4) —CH$_2$CH$_2$—;

including the lower alkanoates thereof.

2. A compound according to claim 1, wherein $W_1$ is $\alpha\text{-H}:\beta\text{-OH}$.

3. A compound according to claim 1, wherein $W_1$ is oxo.

4. A compound according to claim 1, wherein $W_1$ is methylene.

5. A compound according to claim 1, wherein $W_1$ is $\alpha\text{-H}:\beta\text{-H}$.

6. A compound according to claim 5, wherein L is —(CH$_2$)$_n$—, n being 2, 3, or 4, and wherein Q is oxo or $\alpha\text{-OH}:\beta\text{-R}_8$, wherein $R_8$ is limited to hydrogen, methyl, or ethyl.

7. A compound according to claim 1, wherein $W_1$ is $\alpha\text{-}CH_2OH{:}\beta\text{-}H$.

8. A compound according to claim 1, wherein $W_1$ is $\alpha\text{—}OH{:}\beta\text{—}H$.

9. A compound according to claim 8, wherein L is $-(CH_2)_n-$, n being 2, 3, or 4, and wherein Q is oxo or $\alpha\text{-}OH{:}\beta\text{-}R_8$, wherein $R_8$ is hydrogen, methyl, or ethyl.

10. A compound according to claim 9, wherein L is $-CH_2CH_2-$.

11. A compound according to claim 10, wherein $R_5$ and $R_6$ are hydrogen.

12. A compound according to claim 11, wherein s is zero.

13. A compound according to claim 8, wherein X is $-C\equiv C-$.

14. A compound according to claim 8, wherein X is $-CH_2CH_2-$.

15. A compound according to claim 9, wherein X is trans$-CH=CH-$.

16. A compound according to claim 8, wherein X is cis$-CH=CH-$.

17. A compound according to claim 11, wherein s is one.

18. A compound according to claim 17, wherein X is $-CH_2CH_2-$.

19. A compound according to claim 17, wherein X is trans$-CH=CH-$.

20. A compound according to claim 17, wherein X is cis$-CH=CH-$.

21. A compound according to claim 10, wherein $R_5$ and $R_6$ are methyl.

22. A compound according to claim 21, wherein s is zero.

23. A compound according to claim 22, wherein X is $-CH_2CH_2-$.

24. A compound according to claim 22, wherein X is trans$-CH=CH-$.

25. A compound according to claim 22, wherein X is cis$-CH=CH-$.

26. A compound according to claim 10, wherein $R_5$ and $R_6$ are fluoro.

27. A compound according to claim 26, wherein s is zero.

28. A compound according to claim 27, wherein X is $-CH_2CH_2-$.

29. A compound according to claim 27, wherein X is trans$-CH=CH-$.

30. A compound according to claim 8, wherein L is $-CH_2CF_2-$, and wherein Q is oxo or $\alpha OH{:}\beta\text{-}R_8$, wherein $R_8$ is hydrogen, methyl, or ethyl.

31. A compound according to claim 30, wherein $R_5$ and $R_6$ are hydrogen.

32. A compound according to claim 31, wherein s is zero.

33. A compound according to claim 32, wherein X is $-CH_2CH_2-$.

34. A compound according to claim 32, wherein X is trans$-CH=CH-$.

35. A compound according to claim 32, wherein X is cis$-CH=CH-$.

36. A compound according to claim 30, wherein $R_5$ and $R_6$ are methyl.

37. A compound according to claim 36, wherein s is zero.

38. A compound according to claim 37, wherein X is $-CH_2CH_2-$.

39. A compound according to claim 37, wherein X is trans$-CH=CH-$.

40. A compound according to claim 37, wherein X is cis$-CH=CH-$.

41. A 4E compound of the formula wherein $W_1$ is $\alpha\text{-}OH{:}\beta\text{-}H$, $\alpha\text{-}H{:}\beta\text{-}OH$, oxo, methylene, $\alpha\text{-}H{:}\beta\text{-}H$, $\alpha\text{-}CH_2OH{:}\beta\text{-}H$;

wherein L is $-(CH_2)_d-C(R_2)_2$, wherein d is zero to 5, $R_2$ is hydrogen, methyl, or fluoro, being the same or different with the proviso that one $R_2$ is not methyl when the other is fluoro;

wherein Q is oxo, $\alpha\text{-}H{:}\beta\text{-}H$, $\alpha\text{-}OH{:}\beta\text{-}R_8$ or $\alpha\text{-}R_8{:}\beta\text{-}OH$ wherein $R_8$ is hydrogen or alkyl of one to 4 carbon atoms, inclusive; and wherein $R_9$ is hydrogen, methyl, or ethyl, and wherein $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa ($-O-$); wherein Z represents an oxa atom ($-O-$), a valence bond or alkylene of one to 9 carbon atoms, inclusive, with one to 6 carbon atoms, inclusive between $CR_5R_6-$ and the phenyl ring;

wherein T is alkyl of one to 4 carbon atoms, inclusive, fluoro, chloro, trifluoromethyl, or $-OR_7-$, wherein $R_7$ is alkyl of one to 4 carbon atoms, inclusive, and s is zero, one, 2, or 3, with the proviso that not more than two T's are other than alkyl and when s is 2 or 3 the T's are either the same or different; and wherein X is (1) trans$-CH=CH-$, (2) cis$-CH=CH-$, (3) $-C\equiv C-$, or (4) $-CH_2CH_2-$;

including the lower alkanoates thereof.

* * * * *